(12) United States Patent
Fujie et al.

(10) Patent No.: US 8,231,754 B2
(45) Date of Patent: Jul. 31, 2012

(54) COLORING COMPOSITION, THERMAL TRANSFER RECORDING INK SHEET, THERMAL TRANSFER RECORDING METHOD, COLOR TONER, INKJET INK, COLOR FILTER, AND DYE COMPOUND

(75) Inventors: Yoshihiko Fujie, Kanagawa (JP);
Tetsuya Watanabe, Kanagawa (JP);
Hisashi Mikoshiba, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 82 days.

(21) Appl. No.: 12/394,099

(22) Filed: Feb. 27, 2009

(65) Prior Publication Data
US 2009/0218039 A1    Sep. 3, 2009

(30) Foreign Application Priority Data

Feb. 29, 2008    (JP) ................... 2008-049977

(51) Int. Cl.
*B44C 1/17*     (2006.01)
*C07D 339/06*   (2006.01)
*C07D 417/02*   (2006.01)
*C07D 231/10*   (2006.01)
*C07D 275/06*   (2006.01)
*C07D 413/02*   (2006.01)

(52) U.S. Cl. ........ 156/230; 548/159; 548/212; 548/214; 548/311.7; 548/364.4

(58) Field of Classification Search ............... None
See application file for complete search history.

(56) References Cited

U.S. PATENT DOCUMENTS

| | | | | |
|---|---|---|---|---|
| 3,211,748 A | * | 10/1965 | Wizinger et al. ............. | 549/32 |
| 3,725,394 A | * | 4/1973 | Donche et al. ............... | 549/32 |
| 4,985,395 A | * | 1/1991 | Vanmaele et al. ............ | 503/227 |
| 2010/0025642 A1 | * | 2/2010 | Hanaki et al. ................. | 252/588 |
| 2010/0076124 A1 | * | 3/2010 | Yawata et al. ................. | 524/84 |

FOREIGN PATENT DOCUMENTS

| | | | |
|---|---|---|---|
| DD | 208476 | * | 5/1984 |
| EP | 384040 | * | 8/1990 |
| EP | 536647 | * | 4/1993 |
| JP | 2004-22387 | * | 1/2004 |

OTHER PUBLICATIONS

Horiike, T, "New Dyes Containing the 1,3-Benzodithiole Residue", Dyes and Pigments, 6(5), 321-329, 1985.*
Huenig, Siegfried et al., "Azo Dyes by Oxidative Coupling. XXIX. Derivatives of 2-Methyl-1,2-Benzoisothiazolin-3-one, 1,3-Benzodithiol-2-one and 3H-1,2-Benzodithiol-3-one Hydrazones", Justis Liebigs Annalen der Chemie, 754, 46-55, 1971.*

* cited by examiner

*Primary Examiner* — Kamal Saeed
(74) *Attorney, Agent, or Firm* — Sughrue Mion, PLLC

(57) ABSTRACT

An dye compound of the following formula (1):

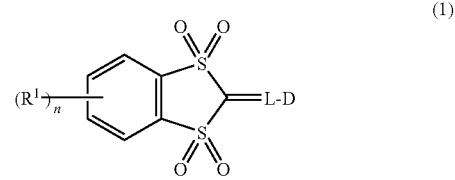

(1)

wherein D represents a substituted or unsubstituted aryl group, or a substituted or unsubstituted heterocyclic group; L represents =$CR^2$—, =N—, or =N—NH—; $R^1$ represents a monovalent substituent; $R^2$ represents a hydrogen atom or a cyano group; n indicates an integer of from 0 to 4; when n is 2 or more, then plural $R^1$'s may be the same or different.

7 Claims, 1 Drawing Sheet

COLORING COMPOSITION, THERMAL TRANSFER RECORDING INK SHEET, THERMAL TRANSFER RECORDING METHOD, COLOR TONER, INKJET INK, COLOR FILTER, AND DYE COMPOUND

BACKGROUND OF THE INVENTION

1. Field of the Invention

The present invention relates to a specific novel dye compound, and a coloring composition, a thermal transfer recording ink sheet, a thermal transfer recording method, a color toner, an inkjet ink and a color filter containing the specific dye compound.

2. Background Art

These days, in particular, a color image-forming material is the mainstream of an image-recording material; and concretely, inkjet-type recording materials, thermal transfer-type recording materials, electrophotographic recording materials, transfer-type silver halide photosensitive materials, printing inks and recording pens are much used. In an image sensor such as CCD as photography machinery and in LCD or PDP as displays, a color filter is used for recording and reproducing color images.

In a color image-recording material and a color filter, used are colorants (dyes, pigments) of three primary colors for an additive mixture process or a subtractive mixture process. At present, however, no one could find a fast colorant that has absorption characteristics capable of realizing a favorable color reproduction range and is durable to various conditions in practical use, and it is strongly desired to improve colorants.

Thermal transfer recording includes a recording system where a thermal transfer material having a thermofusible ink layer formed on a support (base film) is heated with a thermal head to thereby melt the ink for recording on an image-recording material, and a recording system where a thermal transfer material having a transferable dye-containing dye-donating layer formed on a support is heated with a thermal head to thereby thermally diffuse and transfer the dye onto an image-receiving material. In the latter thermal transfer system, the dye transfer rate may be varied by changing the energy to be applied to the thermal head, therefore facilitating gradation recording, and the system is especially advantageous for high-quality full-color recording. However, the transferable dye for use in this system has various limitations, and only an extremely few dyes are known capable of satisfying all the necessary performance requirements.

The performance requirements include, for example, spectral characteristics favorable for color reproduction, easy transferability, fastness to light and heat, fastness to various chemicals, easy producibility, and easy workability to construct thermal transfer recording materials. However, conventional specific dyes that have been proposed as those having spectral characteristics favorable for color reproduction and having fastness to light and heat (for example see Patent JP-A 1-225592 and JP-A 63-189289) could not be on a satisfactory level, and further improvements are strongly desired.

In color copiers and color laser printers to be driven by electrophotography, in general, a toner is widely used that comprises a colorant dispersed in resin particles. The performance requirements for the color toner include absorption characteristics capable of realizing a preferred color reproduction range, especially high transmittance (transparency) required in use in overheat projectors (hereinafter referred to as OHP), and various fastness requirements under environmental conditions in practical use. A toner comprising a pigment colorant dispersed in particles has been proposed (for example, see JP-A 62-157051, JP-A 62-255956 and JP-A 6-118715). The toner of the type may have excellent light fastness, but may readily aggregate as being insoluble and is problematic in point of the transparency reduction and the transmitted color shift. On the other hand, a toner comprising a specific dye as a colorant has also been proposed (for example, see JP-A3-276161, JP-A2-207274 and JP-A 2-207273), and the toner of the type has high transparency and is free from the problem of color shift contrary to the above, but is problematic in point of the light fastness.

An inkjet recording method has been rapidly popularized and is being developed further more, since its material cost is low, it enables high-speed recording, it is noiseless in recording operation, and it facilitates color recording.

The inkjet recording method includes a continuous system of continuously jetting out ink droplets and an on-demand system of jetting out ink droplets in accordance with image information signals; and the jetting system includes a system of jetting out ink droplets under pressure given thereto by a piezo device, a system of jetting out ink droplets by generating bubbles in ink by heat, a system of using ultrasonic waves, and a system of electrostatically sucking and jetting out ink droplets. As the inkjet recording ink, usable is water-base ink, oily ink, or solid (fusible) ink.

The requirements for the colorant to be used in the inkjet recording ink are that it well dissolves or disperses in solvent, it enables high-density recording, its color is good, it is fast to light, heat, active gases in the environment (e.g., oxidizing gas such as NOx, SOx, ozone), it is fast to water and chemicals, it may well fix in image-receiving material and hardly blurs it, it is well storable as ink, it is nontoxic, its purity is high, and it is inexpensive and easily available. However, it is extremely difficult to obtain a colorant that satisfies all these requirements at a high level. In particular, it is strongly desired to obtain a colorant that has a good magenta color tone, has high solubility, and is fast to light, humidity and heat, especially highly fast to light.

A color filter is required to have high transparency, for which, therefore, employed is a dyeing method of coloration with a dye. For example, a method that comprises patterning exposure and development of a dyeable photoresist to form a pattern, and then dyeing it with a filter color dye is successively repeated for all filter colors to produce a color filter. Apart form the dyeing method, a method of using a positive resist may also be employed for producing a color filter. The color filters produced according to these methods may have high transparency and excellent optical properties as using dyes, but their light fastness and heat resistance are limited. Accordingly, a colorant having excellent fastness and having high transparency is desired. On the other hand, a method of using an organic pigment having excellent light fastness and heat resistance in place of dye is widely known, but pigment-containing color filters could hardly have good optical properties like those of dye-containing color filters.

Common to those for use in the above-mentioned applications, the dyes are desired to have the following properties. Specifically, they have a color favorable for color reproduction, they have an optimum spectral absorption, their fastness such as light fastness, moisture fastness, chemical fastness is good, their solubility is high.

For use in thermal transfer recording, dyes having a specific dicyanostyryl skeleton have been proposed (for example, see JP-A 2-579). However, the dyes could not always satisfy the above-mentioned requirements for their properties on a satisfactory level, and further investigations are desired.

SUMMARY OF THE INVENTION

An object of the invention is to provide a novel dye compound having excellent spectral characteristics with sharp absorption and having high fastness, a color composition containing the dye compound, a thermal transfer recording ink sheet containing the dye compound and a thermal transfer recording method. Another object is to provide a color toner, an inkjet ink and a color filter comprising the dye compound.

The present inventors have assiduously studied and, as a result, have found that the above-mentioned objects can be attained by the following constitution:

[1] A dye compound of the following formula (1):

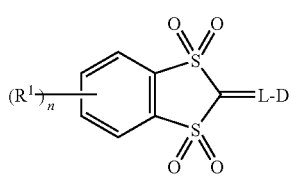

(1)

wherein D represents a substituted or unsubstituted aryl group, or a substituted or unsubstituted heterocyclic group; L represents $=CR^2-$ ($R^2$ represents a hydrogen atom or a cyano group), $=N-$, or $=N-NH-$; $R^1$ represents a monovalent substituent; n indicates an integer of from 0 to 4; when n is 2 or more, then plural $R^1$'s may be the same or different.

[2] The dye compound of the above (1), wherein the dye compound of formula (1) is represented by the following formula (2) or (3):

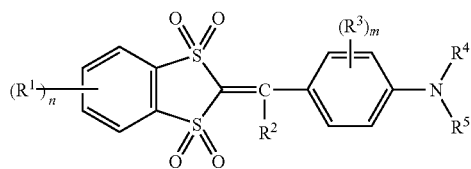

(2)

wherein $R^1$, $R^3$, $R^4$ and $R^5$ each independently represent a monovalent substituent; $R^2$ represents a hydrogen atom or a cyano group; n and m each independently indicate an integer of from 0 to 4; when n is 2 or more, then plural $R^1$'s may be the same or different; when m is 2 or more, then plural $R^3$'s may be the same or different; $R^4$ and $R^5$ may bond to each other to form a cyclic structure; at least one of $R^4$ and $R^5$ may bond to $R^3$ to form a cyclic structure;

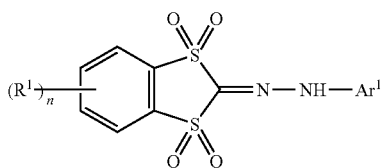

(3)

wherein $R^1$ represents a monovalent substituent; n indicates an integer of from 0 to 4; $Ar^1$ represents a group selected from the following aryl group and heterocyclic group (1); when n is 2 or more, then plural $R^1$'s may be the same or different; Aryl group and heterocyclic group (1):

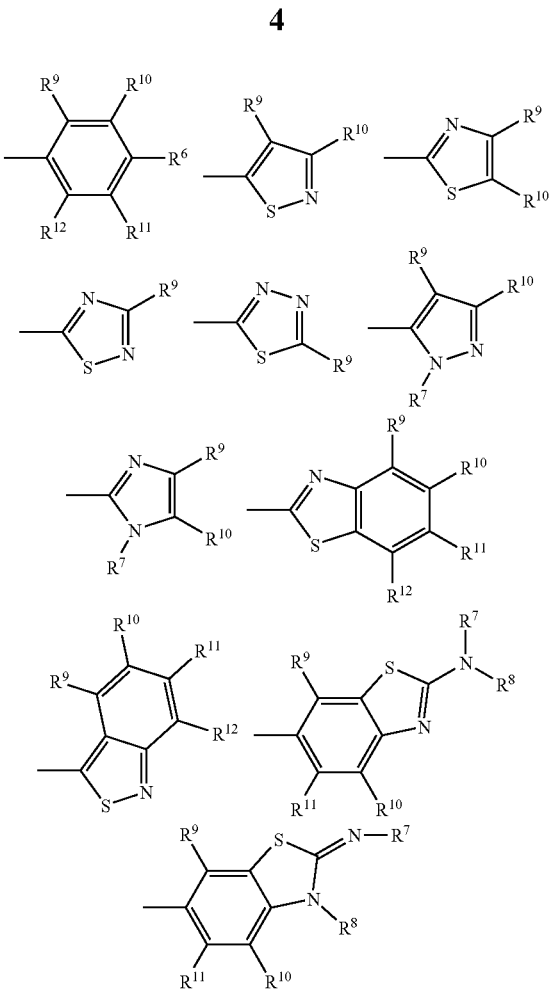

wherein $R^6$ represents a monovalent substituent; $R^7$, $R^8$, $R^9$, $R^{10}$, $R^{11}$ and $R^{12}$ each independently represent a hydrogen atom or a monovalent substituent.

[3] A coloring composition containing the dye compound of the above [1] or [2].

[4] A thermal transfer recording ink sheet containing the dye compound of the above [1] or [2].

[5] A thermal transfer recording method comprising forming an image by use of the thermal transfer recording ink sheet of the above [4] on an image-receiving material comprising a polymer-containing ink-receiving layer on a support.

[6] A color toner containing the dye compound of the above [1] or [2].

[7] An inkjet ink containing the dye compound of the above [1] or [2].

[8] A color filter containing the dye compound of the above [1] or [2].

According to the invention, there are provided a novel dye compound having excellent spectral characteristics with sharp absorption and having extremely high fastness, a thermal transfer ink sheet containing the dye compound and a thermal transfer recording method. Unexpectedly, the novel dye compound has high light fastness and wet heat fastness, for example, as compared with conventional known similar dyes, and therefore can provide a thermal transfer ink sheet and a thermal transfer recording method capable of satisfying excellent color reproducibility in printed samples. Further, the invention provides a color toner, an inkjet ink and a color filter comprising the dye compound.

BEST MODE FOR CARRYING OUT THE INVENTION

Figure 1:
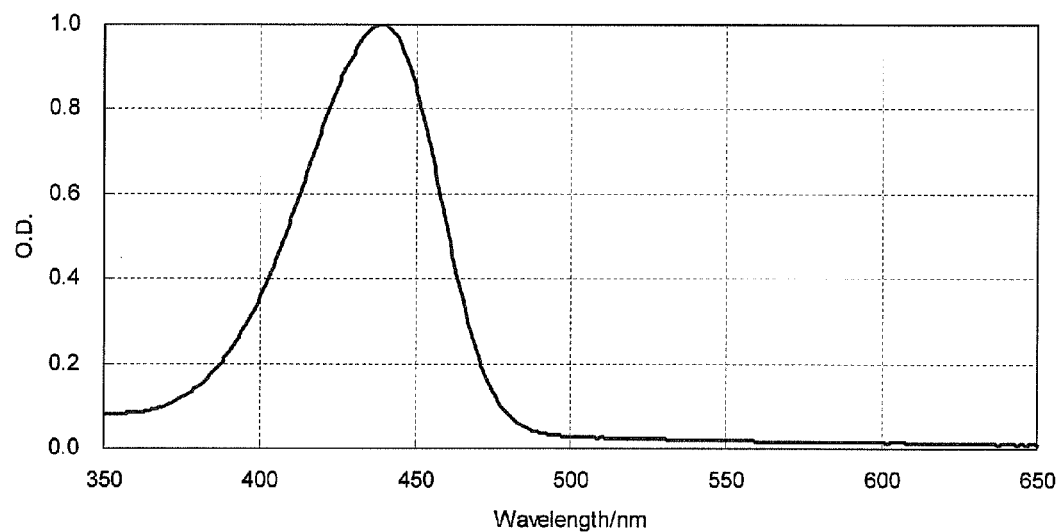
FIG. 1 is a reflection spectrum of the thermal transfer recording image obtained in Example 301.

The thermal transfer recording ink sheet, the color toner, the inkjet ink and the color filter and also the novel dye compound for use in these of the invention are described in detail hereinunder.

The description of the constitutive elements of the invention given hereinunder is for some typical embodiments of the invention, to which, however, the invention should not be limited. In this description, the numerical range expressed by the wording "a number to another number" means the range that falls between the former number indicating the lowermost limit of the range and the latter number indicating the uppermost limit thereof.

[Dye Compound of Formula (1)]

First, the dye compound of formula (1) of the invention is described in detail.

The dye compound of formula (1) is characterized in that the coupling component in the acidic hetero ring/azo dye of a methine dye structure is benzodithiol-1,1,3,3-tetroxide. (The acidic hetero ring as referred to herein is defined by James, The Theory of the Photographic Process, 4th Ed., MacMillan Publishing, 1977, p. 197. The coupling component is defined, for example, by S. Ohkawara, K. Matsuoka, T. Hirashima & T. Kitao, Functional Dye, Kodansha Scientific, 1992, p. 79.) The dye compound having the skeleton is heretofore not known at all.

In formula (1), L represents =$CR^2$— ($R^2$ represents a hydrogen atom or a cyano group), =N—, or =N—NH—.

L is preferably =$CR^2$— ($R^2$ represents a hydrogen atom or a cyano group), or =N—NH—; more preferably L is =CH— or =N—NH—.

In formula (1), n indicates an integer of from 0 to 4. When n is 2 or more, then plural $R^1$'s may be the same or different.

n is preferably from 0 to 3, more preferably from 0 to 2, even more preferably 0 or 1.

In formula (1), $R^1$ represents a mono-valent substituent. The substituent for $R^1$ is not specifically defined. Its typical examples include a halogen atom, an aliphatic group [a saturated aliphatic group (this means an alkyl group, or a cyclic saturated aliphatic group including a cycloalkyl group, a bicycloalkyl group, a crosslinked cyclic saturated hydrocarbon group, a spiro-saturated hydrocarbon group), an unsaturated aliphatic group (this means a linear unsaturated aliphatic group having a double bond or a triple bond, such as an alkenyl group, an alkynyl group; or a cyclic unsaturated aliphatic group including a cycloalkenyl group, a bicycloalkenyl group, a crosslinked cyclic unsaturated hydrocarbon group, a spiro-unsaturated hydrocarbon group)], an aryl group (preferably a phenyl group optionally having a substituent), a heterocyclic group (preferably a 5- to 8-membered, alicyclic, aromatic or heterocyclic ring having an oxygen atom, a sulfur atom or a nitrogen atom as the ring-constitutive atom, and it may be a condensed ring), a cyano group, an aliphatic oxy group (typically an alkoxy group), an aryloxy group, an acyloxy group, a carbamoyloxy group, an aliphatic oxycarbonyloxy group (typically an alkoxycarbonyloxy group, an aryloxycarbonyloxy group), an amino group [including an aliphatic amino group (typically an alkylamino group), an anilino group, a heterocyclic amino group], an acylamino group, an aminocarbonylamino group, an aliphatic oxycarbonylamino group (typically an alkoxycarbonylamino group), an aryloxycarbonylamino group, a sulfamoylamino group, an aliphatic (typically an alkyl) or arylsulfonylamino group, an aliphatic thio group (typically an alkylthio group), an arylthio group, a sulfamoyl group, an aliphatic (typically an alkyl) or arylsulfinyl group, an aliphatic (typically an alkyl) or arylsulfonyl group, an acyl group, an aryloxycarbonyl group, an aliphatic oxycarbonyl group (typically an alkoxycarbonyl group), a carbamoyl group, an aryl or heterocyclic azo group, an aliphatic oxysulfonyl group (typically an alkoxysulfonyl group), an aryloxysulfonyl group, a halogen atom, a hydroxyl group, a nitro group, a carboxyl group, a sulfo group. These groups may be further substituted (for example, with the substituent mentioned in the above for $R^1$).

The substituents of $R^1$, and the substituents which these groups may optionally have are described in more detail hereinunder.

The halogen atom includes a fluorine atom, a chlorine atom, a bromine atom and an iodine atom. Above all, preferred are a chlorine atom and a bromine atom; and more preferred is a chlorine atom.

The aliphatic group is a linear, branched or cyclic aliphatic group; and as so mentioned in the above, the saturated aliphatic group includes an alkyl group, a cycloalkyl group, a bicycloalkyl group; and these may be further substituted. Preferably, the number of the carbon atoms constituting the group is from 1 to 30. Its examples include a methyl group, an ethyl group, an n-propyl group, an isopropyl group, a tert-butyl group, an n-octyl group, an eicosyl group, a 2-chloroethyl group, a 2-cyanoethyl group, a benzyl group, a 2-ethylhexyl group. The cycloalkyl group includes a substituted or unsubstituted cycloalkyl group. For the substituted or unsubstituted cycloalkyl group, the cycloalkyl group preferably has from 3 to 30 carbon atoms. Its examples include a cyclohexyl group, a cyclopentyl group, a 4-n-dodecylcyclohexyl group. The bicycloalkyl group is a substituted or unsubstituted bicycloalkyl group having from 5 to 30 carbon atoms, or that is, a monovalent group derived from a bicycloalkane having from 5 to 30 carbon atoms by removing one hydrogen atom therefrom. Its examples include a bicyclo[1.2.2]heptan-2-yl group, a bicyclo[2.2.2]octan-3-yl group. It further includes a tricyclo structure and more multi-cyclo structures.

The unsaturated aliphatic group is a linear, branched or cyclic unsaturated aliphatic group, including an alkenyl group, an cycloalkenyl group, a bicycloalkenyl group, an alkynyl group. The alkenyl group is a linear, branched or cyclic, substituted or unsubstituted alkenyl group. Preferably, the alkenyl group is an unsubstituted or substituted alkenyl group having from 2 to 30 carbon atoms. Its examples include a vinyl group, an allyl group, a prenyl group, a geranyl group, an oleyl group. The cycloalkenyl group is preferably a substituted or unsubstituted cycloalkenyl group having from 3 to 30 carbon atoms, or that is, a monovalent group derived from a cycloalkene having from 3 to 30 carbon atoms by removing one hydrogen atom therefrom. Its examples include a 2-cyclopenten-1-yl group, a 2-cyclohexen-1-yl group. The bicycloalkenyl group includes a substituted or unsubstituted bicycloalkenyl group. The bicycloalkenyl group is preferably a substituted or unsubstituted bicycloalkenyl group having from 5 to 30 carbon atoms, or that is, a monovalent group derived from a bicycloalkene having one double bond by removing one hydrogen atom therefrom. Its examples include a bicyclo[2.2.1]hept-2-en-1-yl group, a bicyclo[2.2.2]oct-2-en-4-yl group. The alkynyl group is preferably a substituted or unsubstituted alkynyl group having from 2 to 30 carbon atoms, including, for example, an ethynyl group, a propargyl group.

The aryl group is preferably a substituted or unsubstituted aryl group having from 6 to 30 carbon atoms, including, for example, a phenyl group, a p-tolyl group, a naphthyl group, a m-chlorophenyl group, an o-hexadecanoylaminophenyl group. Preferred is a phenyl group optionally having a substituent.

The heterocyclic group is a monovalent group derived from a substituted or unsubstituted, aromatic or non-aromatic heterocyclic compound by removing one hydrogen atom therefrom, and it may form a condensed ring. The heterocyclic group is preferably a 5- or 6-membered heterocyclic group, and the ring-constituting hetero atom is preferably an oxygen atom, a sulfur atom, a nitrogen atom. More preferably, it is a 5- or 6-membered aromatic heterocyclic group having from 3 to 30 carbon atoms. The hetero ring of the heterocyclic group includes a pyridine ring, a pyrazine ring, a pyridazine ring, a pyrimidine ring, a triazine ring, a quinoline ring, an isoquinoline ring, a quinazoline ring, a cinnoline ring, a phthalazine ring, a quinoxaline ring, a pyrrole ring, an indole ring, a furan ring, a benzofuran ring, a thiophene ring, a benzothiophene ring, a pyrazole ring, an imidazole ring, a benzimidazole ring, a triazole ring, an oxazole ring, a benzoxazole ring, a thiazole ring, a benzothiazole ring, an isothiazole ring, a benzisothiazole ring, a thiadiazole ring, an isoxazole ring, a benzisoxazole ring, a pyrrolidine ring, a piperidine ring, a piperazine ring, an imidazolidine ring, a thiazoline ring.

The aliphatic oxy group (typically alkoxy group) includes a substituted or unsubstituted aliphatic oxy group (typically alkoxy group), and preferably has from 1 to 30 carbon atoms. For example, it includes a methoxy group, an ethoxy group, an isopropoxy group, an n-octyloxy group, a methoxyethoxy group, a hydroxyethoxy group, a 3-carboxypropoxy group.

The aryloxy group is preferably a substituted or unsubstituted aryloxy group having from 6 to 30 carbon atoms. Examples of the aryloxy group include a phenoxy group, a 2-methylphenoxy group, a 4-tert-butylphenoxy group, a 3-nitrophenoxy group, a 2-tetradecanoylaminophenoxy group. Preferred is a phenyloxy group optionally having a substituent.

The acyloxy group is preferably a formyloxy group, a substituted or unsubstituted alkylcarbonyloxy group having from 2 to 30 carbon atoms, or a substituted or unsubstituted arylcarbonyloxy group having from 6 to 30 carbon atoms. Examples of the acyloxy group include a formyloxy group, an acetyloxy group, a pivaloyloxy group, a stearoyloxy group, a benzoyloxy group, a p-methoxyphenylcarbonyloxy group.

The carbamoyloxy group is preferably a substituted or unsubstituted carbamoyloxy group having from 1 to 30 carbon atoms. Examples of the carbamoyloxy group include an N,N-dimethylcarbamoyloxy group, an N,N-diethylcarbamoyloxy group, a morpholinocarbonyloxy group, an N,N-di-n-octylaminocarbonyloxy group, an N-n-octylcarbamoyloxy group.

The aliphatic oxycarbonyloxy group (typically alkoxycarbonyloxy group) preferably has from 2 to 30 carbon atoms, and it may have a substituent. For example, it includes a methoxycarbonyloxy group, an ethoxycarbonyloxy group, a tert-butoxycarbonyloxy group, an n-octylcarbonyloxy group.

The aryloxycarbonyloxy group is preferably a substituted or unsubstituted aryloxycarbonyloxy group having from 7 to 30 carbon atoms. Examples of the aryloxycarbonyloxy group include a phenoxycarbonyloxy group, a p-methoxyphenoxycarbonyloxy group, a p-n-hexadecyloxyphenoxycarbonyloxy group. Preferred is a phenoxycarbonyloxy group optionally having a substituent.

The amino group includes an amino group, an aliphatic amino group (typically an alkylamino group), an arylamino group and a heterocyclic amino group. The amino group is preferably a substituted or unsubstituted aliphatic amino group (typically an alkylamino group) having from 1 to 30 carbon atoms, or a substituted or unsubstituted arylamino group having from 6 to 30 carbon atoms. Examples of the amino group include an amino group, a methylamino group, a dimethylamino group, an anilino group, an N-methylanilino group, a diphenylamino group, a hydroxyethylamino group, a carboxyethylamino group, a sulfoethylamino group, a 3,5-dicarboxyanilino group, a 4-quinolylamino group.

The acylamino group is preferably a formylamino group, a substituted or unsubstituted alkylcarbonylamino group having from 1 to 30 carbon atoms, or a substituted or unsubstituted arylcarbonylamino having from 6 to 30 carbon atoms. Examples of the acylamino group include a formylamino group, an acetylamino group, a pivaloylamino group, a lauroylamino group, a benzoylamino group, a 3,4,5-tri-n-octyloxyphenylcarbonylamino group.

The aminocarbonylamino group is preferably a substitute or unsubstituted aminocarbonylamino group having from 1 to 30 carbon atoms. Examples of the aminocarbonylamino group include a carbamoylamino group, an N,N-dimethylaminocarbonylamino group, an N,N-diethylaminocarbonylamino group, a morpholinocarbonylamino group. The term "amino" in this group has the same meaning as that of the "amino" in the above-mentioned amino group.

The aliphatic oxycarbonylamino group (typically alkoxycarbonylamino group) preferably has from 2 to 30 carbon atoms, and may have a substituent. For example, it includes a methoxycarbonylamino group, an ethoxycarbonylamino group, a tert-butoxycarbonylamino group, an n-octadecyloxycarbonylamino group, an N-methyl-methoxycarbonylamino group.

The aryloxycarbonylamino group is preferably a substituted or unsubstituted aryloxycarbonylamino group having from 7 to 30 carbon atoms. Examples of the aryloxycarbonylamino group include a phenoxycarbonylamino group, a p-chlorophenoxycarbonylamino group, a m-n-octyloxyphenoxycarbonylamino group. Preferred is a phenyloxycarbonylamino group optionally having a substituent.

The sulfamoylamino group is preferably a substituted or unsubstituted sulfamoylamino group having from 0 to 30 carbon atoms. Examples of the sulfamoylamino group include a sulfamoylamino group, an N,N-dimethylaminosulfonylamino group, an N-n-octylaminosulfonylamino group.

The aliphatic (typically alkyl) or arylsulfonylamino group is preferably a substituted or unsubstituted aliphatic sulfonylamino group (typically an alkylsulfonylamino group) having from 1 to 30 carbon atoms, a substituted or unsubstituted arylsulfonylamino group having from 6 to 30 carbon atoms (preferably a phenylsulfonylamino group optionally having a substituent). For example, it includes a methylsulfonylamino group, a butylsulfonylamino group, a phenylsulfonylamino group, a 2,3,5-trichlorophenylsulfonylamino group, a p-methylphenylsulfonylamino group.

The aliphatic thio group (typically alkylthio group) is preferably a substituted or unsubstituted alkylthio group having from 1 to 30 carbon atoms. Examples of the alkylthio group include a methylthio group, an ethylthio group, an n-hexadecylthio group.

The aryl thio group is preferably a substituted or unsubstituted aryl thio group having from 6 to 20 carbon atoms.

Examples of the aryl thio group include a phenylthio group, a 1-naphthylthio group, 2-naphthylthio group.

The sulfamoyl group is preferably a substituted or unsubstituted sulfamoyl group having from 0 to 30 carbon atoms. Examples of the sulfamoyl group include an N-ethylsulfamoyl group, an N-(3-dodecyloxypropyl)sulfamoyl group, an N,N-dimethylsulfamoyl group, an N-acetylsulfamoyl group, an N-benzoylsulfamoyl group, an N-(N'-phenylcarbamoyl)sulfamoyl group.

The aliphatic (typically alkyl) or arylsulfinyl group is preferably a substituted or unsubstituted aliphatic sulfinyl group (typically an alkylsulfinyl group) having from 1 to 30 carbon atoms, a substituted or unsubstituted arylsulfinyl group having from 6 to 30 carbon atoms (preferably a phenylsulfinyl group optionally having a substituent). For example, it includes a methylsulfinyl group, an ethylsulfinyl group, a phenylsulfinyl group, a p-methylphenylsulfinyl group.

The aliphatic (typically alkyl) or arylsulfonyl group is preferably a substituted or unsubstituted aliphatic sulfonyl group (typically an alkylsulfonyl group) having from 1 to 30 carbon atoms, a substituted or unsubstituted arylsulfonyl group having from 6 to 30 carbon atoms (preferably a phenylsulfonyl group optionally having a substituent). For example, it includes a methylsulfonyl group, an ethylsulfonyl group, a phenylsulfonyl group, a p-toluenesulfonyl group.

The acyl group is preferably a formyl group, a substituted or unsubstituted aliphatic carbonyl group (typically an alkylcarbonyl group) having from 2 to 30 carbon atoms, a substituted or unsubstituted arylcarbonyl group having from 7 to 30 carbon atoms (preferably a phenylcarbonyl group optionally having a substituent), a substituted or unsubstituted heterocyclic carbonyl group having from 4 to 30 carbon atoms in which the ring bonds to the carbonyl group via its carbon atoms. For example, it includes an acetyl group, a pivaloyl group, a 2-chloroacetyl group, a stearoyl group, a benzoyl group, a p-n-octyloxyphenylcarbonyl group, a 2-pyridylcarbonyl group, a 2-furylcarbonyl group.

The aryloxycarbonyl group is preferably a substituted or unsubstituted aryloxycarbonyl group having from 7 to 30 carbon atoms. Examples of the aryloxycarbonyl group include a phenoxycarbonyl group, an o-chlorophenoxycarbonyl group, an m-nitrophenoxycarbonyl group, a p-tert-butylphenoxycarbonyl group. Preferred is a phenyloxycarbonyl group optionally having a substituent.

The aliphatic oxycarbonyl group (typically alkoxycarbonyl group) preferably has from 2 to 30 carbon atoms, and may have a substituent. For example, it includes a methoxycarbonyl group, an ethoxycarbonyl group, a tert-butoxycarbonyl group, an n-octadecyloxycarbonyl group.

The carbamoyl group is preferably a substituted or unsubstituted carbamoyl group having from 1 to 30 carbon atoms. Examples of the carbamoyl group include a carbamoyl group, an N-methylcarbamoyl group, an N,N-dimethylcarbamoyl group, an N,N-di-n-octylcarbamoyl group, an N-(methylsulfonyl)carbamoyl group.

The aryl or heterocyclic azo group includes, for example, a phenylazo group, a 4-methoxyphenylazo group, a 4-pivaloylaminophenylazo group, a 2-hydroxy-4-propanoylphenylazo group.

The imido group includes, for example, an N-succinimide group, an N-phthalimide group.

The aliphatic oxysulfonyl group (typically an alkoxysulfonyl group) preferably has from 1 to 30 carbon atoms, and may have a substituent. For example, it includes a methoxysulfonyl group, an ethoxysulfonyl group, an n-butoxysulfonyl group, etc.

The aryloxysulfonyl group preferably has from 6 to 12 carbon atoms, and may have a substituent. For example, it includes a phenoxysulfonyl group, a 2-naphthoxyphenyl group, etc.

In addition to these, further mentioned are a hydroxyl group, a cyano group, a nitro group, a sulfo group, a carboxyl group.

These groups may be further substituted, and the substituents for them may be the above-mentioned substituents.

$R^1$ is preferably a substituted or unsubstituted alkyl group having from 1 to 8 carbon atoms, a substituted or unsubstituted aryl group having from 6 to 10 carbon atoms, a substituted or unsubstituted heterocyclic group, a substituted or unsubstituted amino group, or a substituted or unsubstituted alkoxy group having from 1 to 8 carbon atoms, more preferably a substituted or unsubstituted alkyl group having from 1 to 6 carbon atoms, or a substituted or unsubstituted alkoxy group having from 1 to 6 carbon atoms, even more preferably a substituted or unsubstituted alkyl group having from 1 to 4 carbon atoms.

In formula (1), D represents a substituted or unsubstituted aryl group, or a substituted or unsubstituted heterocyclic group. Not specifically defined, the group may be an atomic group necessary for the dye compound of formula (1) to have an absorption in at least one region of a visible region or a near IR region. The visible region as referred to herein is a wavelength region of from 400 to 780 nm; and the near IR region is a wavelength region of from 780 to 2000 nm. "Having an absorption in at least one of a visible region or a near IR region" as referred to herein means that the dye compound of formula (1) has a molar absorption coefficient of at least 1000 in at least one of a visible region or a near IR region.

Typical examples of D are a phenyl group, a naphthyl group, a thiazolyl group, an isothiazolyl group, a 1,2,4-thiadiazolyl group, a 1,3,4-thiadiazolyl group, a pyrazolyl group, an imidazolyl group, an oxazolyl group, a thienyl group, an isoxazolyl group, a benzothiazolyl group, a benzisothiazolyl group, a benzoxazolyl group, a pyridyl group, etc. These groups may be further substituted (for example, with the substituent mentioned hereinabove for $R^1$).

D is preferably a substituted phenyl group, a substituted or unsubstituted thiazolyl group, a substituted or unsubstituted isothiazolyl group, a substituted or unsubstituted 1,2,4-thiadiazolyl group, a substituted or unsubstituted 1,3,4-thiadiazolyl group, a substituted or unsubstituted pyrazolyl group, a substituted or unsubstituted imidazolyl group, a substituted or unsubstituted oxazolyl group, a substituted or unsubstituted isoxazolyl group, a substituted or unsubstituted benzothiazolyl group, or a substituted or unsubstituted benzisothiazolyl group, more preferably a substituted phenyl group, a substituted or unsubstituted thiazolyl group, a substituted or unsubstituted isothiazolyl group, a substituted or unsubstituted pyrazolyl group, a substituted or unsubstituted imidazolyl group, a substituted or unsubstituted oxazolyl group, a substituted or unsubstituted isoxazolyl group, a substituted or unsubstituted benzothiazolyl group, or a substituted or unsubstituted benzisothiazolyl group, even more preferably a substituted phenyl group, a substituted or unsubstituted thiazolyl group, a substituted or unsubstituted isothiazolyl group, a substituted or unsubstituted pyrazolyl group, a substituted or unsubstituted imidazolyl group, a substituted or unsubstituted benzothiazolyl group, or a substituted or unsubstituted benzisothiazolyl group.

Regarding the preferred combination of the substituents (combination of D, L, $R^1$ and n) in the dye compound of formula (1) of the invention, it is desirable that at least one of these substituent is the above-mentioned preferable group, more preferably more various substituents are the above-mentioned preferred groups, most preferably all the substituents are the above-mentioned preferred groups.

Most preferred combinations are the dye compounds of formula (2) or (3) mentioned in the above.

The dye compounds of formulae (2) and (3) are described in detail hereinunder.

[Dye Compound of Formula (2)]

The dye compound of formula (2) is an arylidene dye compound in which the benzodithiol-1,1,3,3-tetroxide is an acidic hetero ring. Since the dye compound of formula (1) is heretofore not known at all, the arylidene dye compound having the characteristic is also heretofore not known at all.

In formula (2), $R^1$, $R^2$ and n have the same meanings as those of $R^1$, $R^2$ and n in formula (1), and their preferred ranges are also the same as in the latter.

In formula (2), m indicates an integer of from 0 to 4. When m is 2 or more, then plural $R^3$'s may be the same or different.

m is preferably from 0 to 3, more preferably from 0 to 2, even more preferably 0 or 1.

In formula (2), $R^3$, $R^4$ and $R^5$ each independently represent a monovalent substituent. The substituent is not specifically defined. Its typical examples are the substituents mentioned hereinabove for $R^1$. These may be further substituted (for example, with the substituent mentioned hereinabove for $R^1$).

$R^3$ is preferably a substituted or unsubstituted alkyl group having from 1 to 8 carbon atoms, a substituted or unsubstituted alkoxy group having from 1 to 8 carbon atoms, a substituted or unsubstituted alkylthio group having from 1 to 8 carbon atoms, a substituted or unsubstituted acylamino group, or a halogen atom, more preferably a substituted or unsubstituted alkyl group having from 1 to 6 carbon atoms, a substituted or unsubstituted alkoxy group having from 1 to 6 carbon atoms, a substituted or unsubstituted alkylthio group having from 1 to 6 carbon atoms, or a halogen atom, even more preferably a substituted or unsubstituted alkyl group having from 1 to 4 carbon atoms, a substituted or unsubstituted alkoxy group having from 1 to 4 carbon atoms, or a halogen atom.

Preferably, $R^4$ and $R^5$ each are independently a substituted or unsubstituted alkyl group having from 1 to 8 carbon atoms, an allyl group, a substituted or unsubstituted aryl group having from 6 to 10 carbon atoms, more preferably a substituted or unsubstituted alkyl group having from 1 to 8 carbon atoms, or an allyl group, even more preferably a substituted or unsubstituted alkyl group having from 1 to 6 carbon atoms.

$R^4$ and $R^5$ may bond to each other to form a cyclic structure; and at least one of $R^4$ and $R^5$ may bond to $R^3$ to form a cyclic structure. The ring to be formed by $R^4$ and $R^5$ bonding to each other includes a morpholine ring, a piperazine ring, a piperidine ring, a pyrrolidine ring. The ring to be formed by at least one of $R^4$ and $R^5$ bonding to $R^3$ includes an octahydroquinolidine ring, a piperidine ring (ring excluding the benzene ring with which the ring is condensed)

Regarding the preferred combination of the substituents in the dye compound of formula (2) of the invention, it is desirable that at least one of these substituent is the above-mentioned preferable group, more preferably more various substituents are the above-mentioned preferred groups, most preferably all the substituents are the above-mentioned preferred groups.

Preferred combinations are as follows: $R^1$ is a substituted or unsubstituted alkyl group having from 1 to 8 carbon atoms, $R^2$ is a hydrogen atom or a cyano group, $R^3$ is a substituted or unsubstituted alkyl group having from 1 to 8 carbon atoms, a substituted or unsubstituted alkoxy group having from 1 to 8 carbon atoms, or a halogen atom, $R^4$ is a substituted or unsubstituted alkyl group having from 1 to 8 carbon atoms, $R^5$ is a substituted or unsubstituted alkyl group having from 1 to 8 carbon atoms, n is from 0 to 2, m is from 0 to 3.

More preferred combinations are as follows: $R^1$ is a substituted or unsubstituted alkyl group having from 1 to 8 carbon atoms, $R^2$ is a hydrogen atom, $R^3$ is a substituted or unsubstituted alkyl group having from 1 to 8 carbon atoms, a substituted or unsubstituted alkoxy group having from 1 to 8 carbon atoms, or a halogen atom, $R^4$ is a substituted or unsubstituted alkyl group having from 1 to 8 carbon atoms, $R^5$ is a substituted or unsubstituted alkyl group having from 1 to 8 carbon atoms, n is from 0 to 2, m is from 0 to 3.

Even more preferred combinations are as follows: $R^1$ is a substituted or unsubstituted alkyl group having from 1 to 6 carbon atoms, $R^2$ is a hydrogen atom, $R^3$ is a substituted or unsubstituted alkyl group having from 1 to 6 carbon atoms, a substituted or unsubstituted alkoxy group having from 1 to 8 carbon atoms, or a halogen atom, $R^4$ is a substituted or unsubstituted alkyl group having from 2 to 6 carbon atoms, $R^5$ is a substituted or unsubstituted alkyl group having from 2 to 6 carbon atoms, n is 0 or 1, m is from 0 to 3.

[Dye Compound of Formula (3)]

The dye compound of formula (3) is an azo dye compound in which the benzodithiol-1,1,3,3-tetroxide is a coupling component. (In this description, the azo dye is expressed as a hydrazo form in the azo-hydrazo tautomer equilibrium thereof, but it may have an azo form.) Since the dye compound of formula (1) is heretofore not known at all, the azo dye compound having the characteristic is also heretofore not known at all.

In formula (3), $R^1$ and n have the same meanings as those of $R^1$ and n in formula (1) and preferred range is also the same as in the latter.

In formula (3), $Ar^1$ is a group selected from the above-mentioned aryl group and heterocyclic group (1).

In the aryl group and the heterocyclic group (1), $R^6$, $R^7$, $R^8$, $R^9$, $R^{10}$, $R^{11}$ and $R^{12}$ each independently represent a hydrogen atom or a monovalent substituent. The substituent is not specifically defined. Its typical examples area halogen atom, an aliphatic group [a saturated aliphatic group (this means an alkyl group, or a cyclic saturated aliphatic group including a cycloalkyl group, a bicycloalkyl group, a bridged cyclic saturated hydrocarbon group or a spiro-saturated hydrocarbon group), an unsaturated aliphatic group (having a double bond or a triple bond, this means a linear unsaturated aliphatic group such as an alkenyl group or an alkynyl group, or a cyclic unsaturated aliphatic group including a cycloalkenyl group, a bicycloalkenyl group, a bridged cyclic unsaturated hydrocarbon group or a spiro-unsaturated hydrocarbon group)], an aryl group (preferably a phenyl group optionally having a substituent), a heterocyclic group (preferably a 5- to 8-membered ring containing an oxygen atom, a sulfur atom or a nitrogen atom as the ring-constituting atom, and optionally condensed with an alicyclic ring, an aromatic ring or a heterocyclic ring), a cyano group, an aliphatic oxy group (typically an alkoxy group), an aryloxy group, an acyloxy group, a carbamoyloxy group, an aliphatic oxycarbonyloxy group (typically an alkoxycarbonyloxy group), an aryloxycarbonyloxy group, an amino group [including an aliphatic amino group (typically an alkylamino group), anilino group and heterocyclic amino group], an acylamino group, an aminocarbonylamino group, an aliphatic oxycarbonylamino group (typically an alkoxycarbonylamino group), an aryloxycarbonylamino group, a sulfamoylamino group, an aliphatic (typically alkyl) or arylsulfonylamino group, an aliphatic thio group (typically an alkylthio group), an arylthio group, a sulfamoyl group, an aliphatic (typically alkyl) or arylsulfinyl group, an aliphatic (typically alkyl) or arylsulfonyl group, an acyl group, an aryloxycarbonyl group, an aliphatic oxycarbonyl group (typically an alkoxycarbonyl group), a carbamoyl group, an aryl or heterocyclic azo group, an imido group, an aliphatic oxysulfonyl group (typically an alkoxysulfonyl group), an aryloxysulfonyl group, a hydroxyl group, a nitro group, a carboxyl group, a sulfo group. These groups may be further substituted (for example, with the substituent mentioned hereinabove for $R^1$).

$R^6$ is preferably a substituted or unsubstituted amino group, a substituted or unsubstituted alkoxy group having from 1 to 8 carbon atoms, a substituted or unsubstituted alkylthio group having from 1 to 8 carbon atoms, a substituted or unsubstituted alkoxycarbonyl group having from 1 to 8 carbon atoms, a substituted or unsubstituted aryloxycarbonyl group having from 6 to 10 carbon atoms, a substituted or unsubstituted carbamoyl group, a cyano group, or a nitro group, more preferably a substituted or unsubstituted amino group, a substituted or unsubstituted alkoxy group having from 1 to 8 carbon atoms, a substituted or unsubstituted alkylthio group having from 1 to 8 carbon atoms, a substituted or unsubstituted alkoxycarbonyl group having from 1 to 8 carbon atoms, a substituted or unsubstituted aryloxycarbonyl group having from 6 to 10 carbon atoms, a cyano group, or a nitro group, particularly preferably a substituted or unsubstituted amino group, a substituted or unsubstituted alkoxy group having from 1 to 8 carbon atoms, a substituted or unsubstituted alkylthio group having from 1 to 8 carbon atoms, a substituted or unsubstituted alkoxycarbonyl group having from 1 to 8 carbon atoms, a cyano group, or a nitro group.

Preferably, $R^7$ and $R^8$ are each independently a hydrogen atom, a substituted or unsubstituted alkyl group having from 1 to 8 carbon atoms, a substituted or unsubstituted aryl group having from 6 to 10 carbon atoms, or a substituted or unsubstituted heterocyclic group, more preferably a hydrogen atom, a substituted or unsubstituted alkyl group having from 1 to 8 carbon atoms, or a substituted or unsubstituted aryl group having from 6 to 10 carbon atoms, even more preferably a hydrogen atom, or a substituted or unsubstituted alkyl group having from 1 to 8 carbon atoms.

Preferably, $R^9$, $R^{10}$, $R^{11}$ and $R^{12}$ are each independently a hydrogen atom, a substituted or unsubstituted alkyl group having from 1 to 8 carbon atoms, a substituted or unsubstituted alkoxy group having from 1 to 8 carbon atoms, a substituted or unsubstituted aryl group having from 6 to 10 carbon atoms, a substituted or unsubstituted heterocyclic group, a substituted or unsubstituted acyl group, a substituted or unsubstituted alkoxycarbonyl group having from 1 to 8 carbon atoms, a substituted or unsubstituted amino group, a cyano group, a carbamoyl group, or a substituted or unsubstituted sulfo group, more preferably a hydrogen atom, a substituted or unsubstituted alkyl group having from 1 to 8 carbon atoms, a substituted or unsubstituted alkoxy group having from 1 to 8 carbon atoms, a substituted or unsubstituted phenyl group, a substituted or unsubstituted heterocyclic group, a substituted or unsubstituted acyl group, a substituted or unsubstituted alkoxycarbonyl group having from 1 to 8 carbon atoms, a substituted or unsubstituted amino group, a cyano group, a carbamoyl group, or a substituted or unsubstituted sulfo group, even more preferably a hydrogen atom, a substituted or unsubstituted alkyl group having from 1 to 8 carbon atoms, a substituted or unsubstituted phenyl group, a substituted or unsubstituted heterocyclic group, a substituted or unsubstituted alkoxycarbonyl group having from 1 to 8 carbon atoms, a cyano group, or a carbamoyl group.

Regarding the preferred combination of the substituents in the dye compound of formula (3) of the invention, it is desirable that at least one of these substituent is the above-mentioned preferable group, more preferably more various substituents are the above-mentioned preferred groups, most preferably all the substituents are the above-mentioned preferred groups.

Preferred combinations are as follows: $Ar^1$ is a phenyl group having a substituent, a substituted or unsubstituted isothiazolyl group, or a substituted or unsubstituted benzothiazolyl group, $R^1$ is a substituted or unsubstituted alkyl group having from 1 to 4 carbon atoms, and n is from 0 to 2.

More preferred combinations are as follows: $Ar^1$ is a phenyl group having a substituent, a substituted or unsubstituted isothiazolyl group, or a substituted or unsubstituted benzothiazolyl group, $R^1$ is a substituted or unsubstituted alkyl group having from 1 to 4 carbon atoms, and n is 0 or 1.

Even more preferred combinations are as follows: $Ar^1$ is a phenyl group having a substituent, or a substituted or unsubstituted benzothiazolyl group, $R^1$ is a substituted or unsubstituted alkyl group having from 1 to 4 carbon atoms, and n is 0 or 1.

The molecular weight of the dye compound of formula (1) to (3) is preferably at most 600, more preferably at most 500 from the viewpoint of the thermal diffusibility thereof.

Specific examples (Y-1) to (Y-25) of the dye compound of formula (1) of the invention are shown below, to which, however, the invention should not be limited.

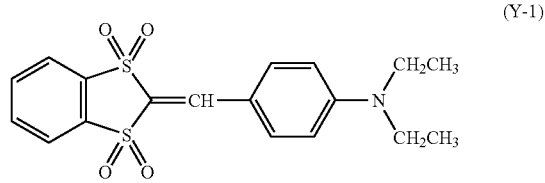

(Y-1)

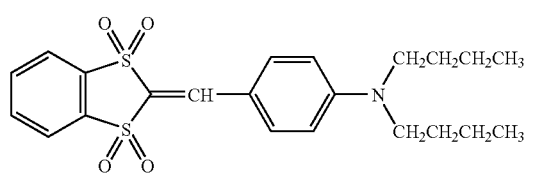

(Y-2)

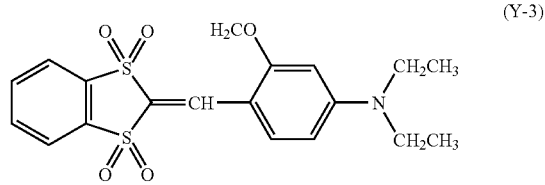

(Y-3)

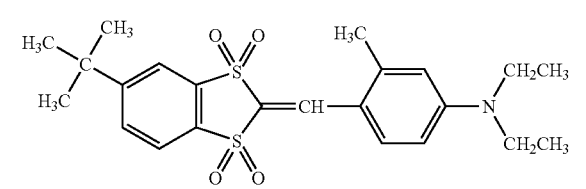

(Y-4)

-continued (Y-5) (Y-6) (Y-7) (Y-8) (Y-9) (Y-10) (Y-11) (Y-12) (Y-13) (Y-14) (Y-15) (Y-16) (Y-17) (Y-18) (Y-19) (Y-20)

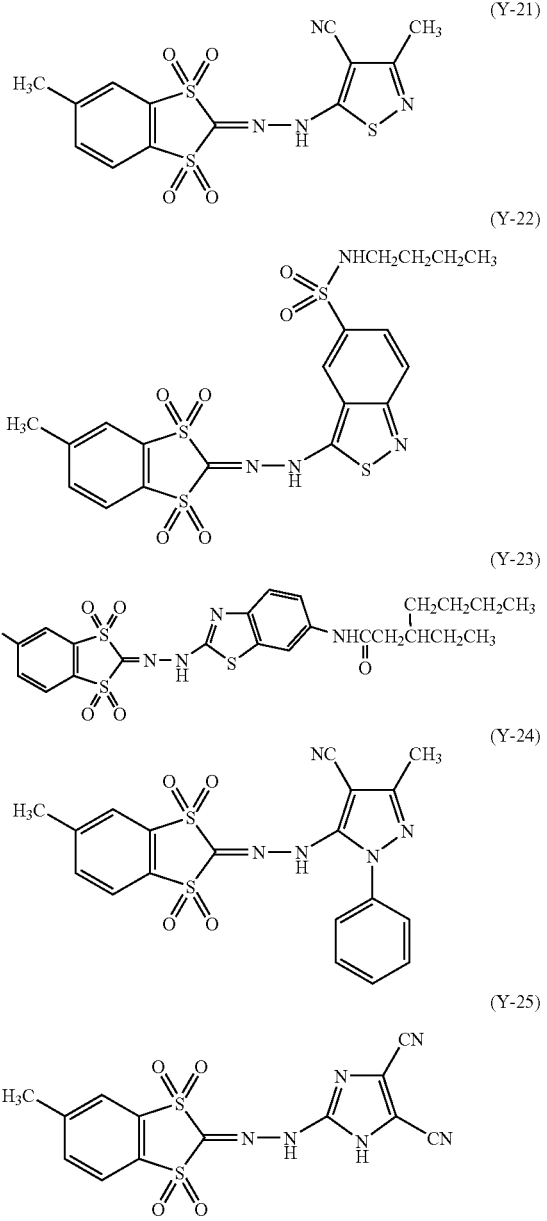

These dye compounds can be produced according to conventional known methods. The methine dye of formula (2) can be produced, for example, through dehydrating condensation of a benzodithiol-1,1,3,3-tetroxide derivative with a benzaldehyde derivative. The azo dye of formula (3) can be produced through ordinary diazocoupling reaction. Concretely, these are disclosed in Examples given hereinunder.

(Benzodithiol-1,1,3,3-tetroxide derivatives can be produced according to the method described in Tetrahedron, Vol. 44, No. 22 (1988), p. 6855.)

The dye compound of the invention is preferably used as a yellow color of three primary colors.

The maximum absorption wavelength of the dye compound of the invention preferably falls within a range of from 400 to 500 nm, more preferably from 420 to 470 nm.

[Coloring Composition]

The coloring composition of the invention is characterized by containing any one of the dye compound of formula (1) to (3) of the invention. The coloring composition in this description is directed to thermal transfer recording ink sheets, inkjet inks, color toners, color filters, writing pens, color plastics, and other ink liquids.

The coloring composition of the invention is especially effectively used for thermal transfer recording ink sheets, inkjet inks, color toners, and color filters.

[Thermal Transfer Recording Ink Sheet]

The thermal transfer recording ink sheet of the invention is characterized by containing any one of the dye compound of formula (1) to (3). The thermal transfer recording ink sheet generally has a structure with a dye-donating layer formed on a support, in which the dye-donating layer contains any one of a dye compound of formula (1) to (3). The thermal transfer recording ink sheet of the invention may be produced as follows: any one of a dye compound of formula (1) to (3) is dissolved in a solvent along with a binder therein or dispersed as particles in a solvent, thereby preparing an ink liquid, then the ink liquid is applied onto a support and suitably dried to form a dye-donating layer thereon. In addition to the dye compound of formula (1) to (3), the other dye may be used.

In case where the invention is applied to thermal transfer recording material that enables full-color image recording, it is desirable that a cyan ink sheet containing a thermal diffusible cyan dye capable of forming cyan images, a magenta ink sheet containing a thermal diffusible magenta dye capable of forming magenta images, and a yellow ink sheet containing a thermal diffusible yellow dye capable of forming yellow images are formed successively on a support. If desired, an ink sheet containing a black image-forming substance may be further formed.

As the thermal diffusible cyan dye-containing cyan ink sheet for forming cyan images, for example, preferably used are those described in JP-A 3-103477, 3-150194. As the thermal diffusible magenta dye-containing magenta ink sheet for forming magenta images, for example, preferably used are those described in JP-A 2-123166. As the thermal diffusible yellow dye-containing yellow ink sheet for forming yellow images, for example, preferably used are those described in JP-A 1-225592.

(Support)

As the support of the thermal transfer recording ink sheet of the invention, any ordinary one heretofore used as a support for ink sheets may be suitably selected and used. For example, the material described in JP-A 7-137466, paragraph [0050] may be favorably used. The thickness of the support is preferably from 2 to 30 μm.

(Dye-Donating Layer)

Not specifically defined, the binder resin usable in the dye-donating layer of the thermal transfer recording ink sheet of the invention may be any one having high heat resistance and not interfering with the transference of any one of the dye compound of formula (1) to (3) or the other dye into an image-receiving material when heated. For example, its preferred examples are described in JP-A 7-137466, paragraph [0049]. The solvent for dye-donating layer formation may also be any conventional known one; and those described in JP-A 7-137466, Examples are favorably used also herein.

The content of any one of the dye compound of formula (1) to (3) in the dye-donating layer is preferably from 0.03 to 1.0 g/m², more preferably from 0.1 to 0.6 g/m². The thickness of the dye-donating layer is preferably from 0.2 to 5 μm, more preferably from 0.4 to 2 μm.

(Functional Layer)

The thermal transfer recording ink sheet of the invention may have any other layer than the dye-donating layer within a range not too much detracting from the effect of the invention. For example, an interlayer may be provided between the support and the dye-donating layer; or a back layer may be provided on the surface of the support opposite to the side of the dye-donating layer (this is hereinafter referred to as "back surface"). The interlayer includes, for example, an undercoating layer, and a diffusion-preventing layer for preventing any one of the dye compound of formula (1) to (3) or the other dye from diffusing toward the support (hydrophilic barrier layer). The back layer is, for example, a heat-resistant slip layer, which is for preventing a thermal head from sticking to the ink sheet.

[Thermal Transfer Recording]

In thermal transfer recording by the use of the thermal transfer recording ink sheet of the invention, a heating unit such as a thermal head and an image-receiving material are used as combined. Specifically, heat energy is applied to the ink sheet from a thermal head according to an image recording signal, and any one of the dye compound of formula (1) to (3) in the part having received the heat energy is transferred to and fixed in an image-receiving material to attain image recording. The image-receiving material generally has a constitution with a polymer-containing ink-receiving layer formed on a support. As the constitution and the constitutive components of the image-receiving material, for example, preferably used are those described in JP-A 7-137466, paragraphs [0056] to [0074]

[Color Toner]

The color toner of the invention is characterized by containing any one of the dye compound of formula (1) to (3). As the binder resin for color toner into which any one of the dye compound of formula (1) to (3) of the invention is introduced, usable is any and every binder for general use in toner. For example, it includes styrene resin, acrylic resin, styrene/acrylic resin, polyester resin. For the purpose of improving the flowability of the toner and for static control thereof, an inorganic fine powder or organic fine particles may be added to the toner as external additives. Preferably used are silica particles and titania particles of which the surfaces are processed with an alkyl group-containing coupling agent or the like. Preferably, the particles have a number-average primary particle size of from 10 to 500 nm; and also preferably, the particles are added to the toner in an amount of from 0.1 to 20% by mass.

As the lubricant, any and every lubricant heretofore used in toner may be used herein. Concretely, it includes olefins such as low-molecular-weight polypropylene, low-molecular-weight polyethylene, ethylene-propylene copolymer; and microcrystalline wax, carnauba wax, Sasol wax, paraffin wax. Preferably, the lubricant is added to the toner in an amount of from 1 to 5% by mass.

If desired, a charge-controlling agent may be added to the toner, and it is preferably colorless from the viewpoint of the colorability of the toner. For example, herein usable are those having a quaternary ammonium salt structure or a calixarene structure.

The carrier may be any of a non-coated carrier formed of magnetic material particles alone of iron, ferrite or the like; or a resin-coated carrier prepared by coating the surfaces of magnetic material particles with resin or the like. Regarding the mean particle size thereof, the carrier preferably has a volume-average particle size of from 30 to 150 μm.

The image-forming method to which the toner of the invention is applicable is not specifically defined. For example, the toner is applicable to an image-forming method that comprises repeatedly forming a color image on a photoreceptor followed by transferring it; and a color image-forming method that comprises transferring an image formed on a photoreceptor successively onto an intermediate transfer medium thereby forming a color image on the intermediate transfer medium, followed by transferring the image onto an image-forming member such as paper.

[Inkjet Ink]

The inkjet ink of the invention is characterized by containing any one of the dye compound of formula (1) to (3). The ink of the invention may be produced by dissolving and/or dispersing any one of the dye compound of formula (1) to (3) in an oleophilic medium or an aqueous medium, and preferably an aqueous medium is used. The ink of the invention contains the dye having excellent spectral characteristics and fastness as so mentioned in the above, and is therefore favorably used as an inkjet recording ink. If desired, other additives may be added to the ink within a range not detracting from the effect of the invention. The additives may be known additives, including, for example, a drying inhibitor (wetting agent), an antifading agent, a emulsion stabilizer, a penetration promoter, a UV absorbent, a preservative, an antifungal agent, a pH controlling agent, a surface tension controlling agent, a defoaming agent, a viscosity controlling agent, a dispersant, a dispersion stabilizer, a rust inhibitor, a chelating agent. In general, these various additives are added to the dye dispersion after its preparation, but as the case may be, they may be added to an oily phase or an aqueous phase in preparing the dye dispersion.

The drying inhibitor is favorably used for the purpose of preventing the inkjet ink from drying at the ink-jetting orifice of the nozzle used in an inkjet recording system.

The drying inhibitor is preferably a water-soluble organic solvent having a vapor pressure lower than water. Its concrete examples include polyalcohols such as typically ethylene glycol, propylene glycol, diethylene glycol, polyethylene glycol, thiodiglycol, dithiodiglycol, 2-methyl-1,3-propanediol, 1,2,6-hexanetriol, acetylene glycol derivative, glycerin, trimethylolpropane; polyalcohol lower alkyl ethers such as ethylene glycol monomethyl (or ethyl) ether, diethylene glycol monomethyl (or ethyl) ether, triethylene glycol monoethyl (or butyl) ether; heterocyclic compounds such as 2-pyrrolidone, N-methyl-2-pyrrolidone, 1,3-dimethyl-2-imidazolidinone, N-ethylmorpholine; sulfur-containing compounds such as sulfolane, dimethyl sulfoxide, 3-sulfolene; polyfunctional compounds such as diacetone alcohol, diethanolamine; and urea derivatives. Of those, more preferred are polyalcohols such as glycerin, diethylene glycol. One or more of the above drying inhibitors may be used either singly or as combined. The drying inhibitor may be in the ink preferably in an amount of from 10 to 50% by mass.

The penetration promoter is favorably used for the purpose of more rapidly penetrating the inkjet ink into paper. As the penetration promoter, usable are alcohols such as ethanol, isopropanol, butanol, di(tri) ethylene glycol monobutyl ether, 1,2-hexanediol; sodium laurylsulfate, sodium oleate, nonionic surfactant. When the agent is in the ink in an amount of from 5 to 30% by mass, then it is generally sufficiently effective. Preferably, the agent is used in an amount not causing print blur and print through.

The UV absorbent is used for the purpose of improving the image storability. The UV absorbent includes benzotriazole compounds as in JP-A 58-185677, 61-190537, 2-782, 5-197075, 9-34057; benzophenone compounds as in JP-A 46-2784, 5-194483, U.S. Pat. No. 3,214,463; cinnamic acid compounds as in JP-B 48-30492, 56-21141, JP-A 10-88106; triazine compounds as in JP-A 4-298503, 8-53427, 8-239368, 10-182621, JP-T 8-501291; and also the compounds described in Research Disclosure No. 24239, and compounds capable of absorbing UV rays to emit fluorescent light, or that is, fluorescent brighteners such as typically stilbene compounds and benzoxazole compounds.

The antifading agent is used for the purpose of improving the image storability. As the antifading agent, usable are various organic or metal complex-type antifading agents. The organic antifading agent includes hydroquinones, alkoxyphenols, dialkoxyphenols, phenols, anilines, amines, indanes, chromans, alkoxyanilines, and heterocyclic compounds; and the metal complex includes nickel complexes and zinc complexes. More concretely, herein usable are the compounds described in the patent references cited in Research Disclosure No. 17643, Items VII-I to J, ibid., No. 15162, ibid., No. 18716, page 650, left column, ibid., No. 36544, page 527, ibid., No. 307105, page 872, ibid., No. 15162; and the compounds falling within the scope of the typical compounds of the formula and the examples of the compounds described in JP-A 62-215272, pp. 127 to 137.

The rust inhibitor includes sodium dehydroacetate, sodium benzoate, sodium pyridinethione-1-oxide, ethyl p-hydroxybenzoate, 1,2-benzisothiazolin-3-one and its salts. Preferably, this is in the ink in an amount of from 0.02 to 1.00% by mass.

As the pH controlling agent, usable are neutralizing agents (organic base, inorganic alkali). For the purpose of improving the storage stability of the inkjet ink, the pH controlling agent is preferably added to the inkjet ink so that the ink could have a pH of from 6 to 10, more preferably from 7 to 10.

The surface tension controlling agent may be a nonionic, cationic or anionic surfactant. Preferably, the surface tension of the inkjet ink containing the coloring composition of the invention is from 20 to 60 mN/m, more preferably from 25 to 45 mN/m. The viscosity of the inkjet ink of the invention is preferably at most 30 mPa·s, more preferably so controlled as to be at most 20 mPa·s.

Preferred examples of the surfactant include anionic surfactants such as fatty acid salts, alkylsulfate ester salts, alkylbenzenesulfonic acid salts, alkylnaphthalenesulfonic salts, dialkylsulfosuccinic acid salts, alkylphosphate ester salts, naphthalenesulfonic acid/formalin condensates, polyoxyethylene alkylsulfate ester salts; and nonionic surfactants such as polyoxyethylene alkyl ethers, polyoxyethylene alkylaryl ethers, polyoxyethylene fatty acid esters, sorbitan fatty acid esters, polyoxyethylene sorbitan fatty acid esters, polyoxyethylene alkylamines, glycerin fatty acid esters, oxyethylene-oxypropylene block copolymers. Also preferred are SURFYNOLS (trade name by Air Products & Chemicals) that are acetylene-type polyoxyethylene oxide surfactants. Also preferred are amine oxide-type ampholytic surfactants such as N,N-dimethyl-N-alkylamine oxide. Further usable herein are the surfactants described in JP-A 59-157636, pp. 37-38, and Research Disclosure No. 308119 (1989).

As the defoaming agent, optionally used herein are fluorine compounds, silicone compounds, and chelating agents such as EDTA.

In case where any one of the dye compound of formula (1) to (3) is dispersed in an aqueous medium, it is desirable that coloring particles containing the compound and an oil-soluble polymer are dispersed in an aqueous medium as in JP-A 11-286637, 2001-240763, 2001-262039, 2001-247788, or any one of the dye compound of formula (1) to (3) dissolved in a high-boiling-point organic solvent is dispersed in an aqueous medium as in JP-A 2001-262018, 2001-240763, 2001-335734, 2002-80772. Regarding the concrete method of dispersing any one of the dye compound of formula (1) to (3) in an aqueous medium, as well as the oil-soluble polymer, the high-boiling-point organic solvent and the additives to be used, and their amount, those described in the above-mentioned patent references are employable herein. As the case may be, the bisazo compound may be dispersed as fine particles directly as it is solid. In dispersing them, a dispersant and a surfactant may be used.

As the dispersing device, usable are simple stirrers, and also impellers, in-line stirrer mills (e.g., colloid mill, ball mill, sand mill, attritor, roll mill, agitator mill), ultrasonic stirrers, high-pressure emulsification dispersers (high-pressure homogenizers; as commercial devices, available are Gaulin homogenizer, Microfluidizer, DeBEE 2000 (by BEE International)). Regarding the method of preparing the above-mentioned inkjet recording ink, its details are described also in JP-A 5-148436, 5-295312, 7-97541, 7-82515, 7-118584, 11-286637, 2001-271003, in addition to the above-mentioned patent references; and these descriptions are applicable to the preparation of the inkjet recording ink of the invention.

As the aqueous medium, usable is a mixture comprising water as the main ingredient and optionally containing a water-miscible organic solvent added thereto. Examples of the water-miscible organic solvent include alcohols (e.g., methanol, ethanol, n-propanol, isopropanol, butanol, isobutanol, sec-butanol, t-butanol, pentanol, hexanol, cyclohexanol, benzyl alcohol), polyalcohols (e.g., ethylene glycol, diethylene glycol, triethylene glycol, polyethylene glycol, propylene glycol, dipropylene glycol, polypropylene glycol, butylene glycol, hexanediol, pentanediol, glycerin, hexanetriol, thiodiglycol), glycol derivatives (e.g., ethylene glycol monomethyl ether, ethylene glycol monoethyl ether, ethylene glycol monobutyl ether, diethylene glycol monomethyl ether, diethylene glycol monobutyl ether, propylene glycol monomethyl ether, propylene glycol monobutyl ether, dipropylene glycol monomethyl ether, triethylene glycol monomethyl ether, ethylene glycol diacetate, ethylene glycol monomethyl ether acetate, triethylene glycol monomethyl ether, triethylene glycol monoethyl ether, ethylene glycol monophenyl ether), amines (e.g., ethanolamine, diethanolamine, triethanolamine, N-methyldiethanolamine, N-ethyldiethanolamine, morpholine, N-ethylmorpholine, ethylenediamine, diethylenetriamine, triethylenetetramine, polyethyleneimine, tetramethylpropylenediamine), and other polar solvents (e.g., formamide, N,N-dimethylformamide, N,N-dimethylacetamide, dimethyl sulfoxide, sulfolane, 2-pyrrolidone, N-methyl-2-pyrrolidone, N-vinyl-2-pyrrolidone, 2-oxazolidone, 1,3-dimethyl-2-imidazolidinone, acetonitrile, acetone). Two or more of the above-mentioned water-miscible organic solvents may be combined for use herein.

[Color Filter]

The color filter of the invention is characterized by containing any one of the dye compound of formula (1) to (3). For producing the color filter, employable is a method of first forming a pattern with a photoresist and then dying it; or a method of forming a pattern with a photoresist to which a colorant is added, as in JP-A 4-163552, 4-128703, 4-175753. As the method of introducing any one of the dye compound of formula (1) to (3) into the color filter of the invention, any of the above methods is employable, but preferred is the method described in JP-A 4-175753, 6-35182. The method comprises applying a positive photoresist composition containing a thermosetting resin, a quinonediazide compound, a crosslinking agent, a colorant and a solvent, onto a support, then exposing it through a mask, developing the exposed area to form a positive resist pattern, then exposing the entire surface of the positive resist pattern to light, and thereafter curing the thus-exposed positive resist pattern to produce a color filter. Also employable is a method of forming a black matrix in an ordinary manner thereby obtaining an RGB primary color filter or an Y.M.C complementary color filter.

For the thermosetting resin, the quinonediazide compound, the crosslinking agent and the solvent to be used in the above and their amount, preferred are those described in the above-mentioned patent references.

EXAMPLES

The characteristics of the invention are described more concretely with reference to Production Examples and Examples given below.

In the following Examples, the material used, its amount and the ratio, the details of the treatment and the treatment process may be suitably modified or changed not overstepping the scope of the invention. Accordingly, the invention should not be limitatively interpreted by the Examples mentioned below.

Example 101

Production of Compound (Y-1)

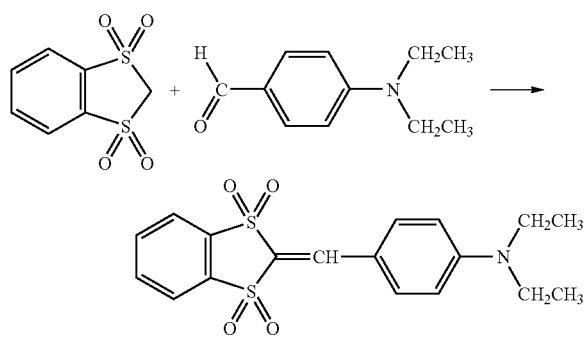

Benzodithiol-1,1,3,3-tetroxide (1.09 g, 5 mmol), 4-(diethylamino)benzaldehyde (1.06 g, 6 mmol) and ammonium acetate (100 mg) were heated under reflux in n-butanol for 24 hours. The reaction liquid was poured into water, then extracted with ethyl acetate, and the extract was concentrated with a rotary evaporator. The residue was purified through silica gel column chromatography to give a yellow solid of the dye compound of Example 101, Compound (Y-1) (0.54 g, yield 29%).

$^1$H NMR (CDCl$_3$) δ (ppm)=1.25 (t, 6H), 3.5 (m, 4H), 6.7 (d, 2H), 7.7 (s, 1H), 7.8-7.9 (dd, 2H).

λmax of the dye compound of Example 101 in ethyl acetate solution was 421 nm.

Example 102

Production of Compounds (Y-15)

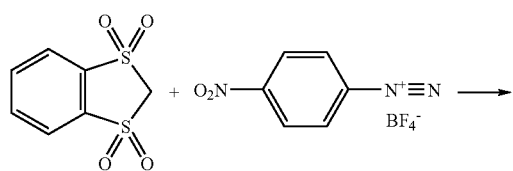

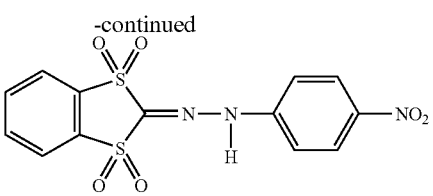

Benzodithiol-1,1,3,3-tetroxide (0.65 g, 3 mmol) was dissolved in methanol (10 mL), and cooled to 0° C. 4-Nitrobenzenediazonium tetrafluoroborate (0.71 g, 3 mmol) was added to it, and then sodium acetate (2.0 g) was added thereto, and stirred at 0° C. for 1 hour and then stirred at room temperature for 2 hours. The reaction liquid was poured into dilute hydrochloric acid, and the precipitated solid was collected through filtration. The collected solid was purified through column chromatography to give an orange solid of the dye compound of Example 102, Compound (Y-15) (0.21 g, yield 18%). λmax of the dye compound of Example 102 in ethyl acetate (1% triethylamine) solution was 362 nm.

Example 103 to 105

Production of Compounds (Y-2), (Y-3) and (Y-5)

Compounds (Y-2), (Y-3) and (Y-5) were produced according to the method of the above Production Example. Other compounds than the compounds may also be produced according to the method of the above-mentioned Production Example from the chemical viewpoint.

<Evaluation of Maximum Absorption Wavelength>

The thus-obtained dyes of Examples 101 to 105 were analyzed absorption spectrometry in an ethyl acetate solution (concentration: 1×10$^{-6}$ mol/L, optical path length: 10 mm). The data of the maximum absorption wavelength of the compounds are shown in the following Table 1.

TABLE 1

| Dye | Maximum Absorption Wavelength (nm) |
|---|---|
| Example 101 | 421 |
| Example 102 | 362 |
| Example 103 | 421 |
| Example 104 | 429 |
| Example 105 | 424 |

Example 201

Construction of Thermal Transfer Recording Ink Sheet

A polyester film (Lumirror, trade name by Toray) having a thickness of 6.0 μm and processed for heat-resistant lubrication with a thermosetting acrylic resin (thickness 1 μm) on its back was used as a support. Using a wire bar coater, a dye-donating layer-forming coating composition comprising the dye compound of the invention produced in Examples 101 (Compound (Y-1)) mentioned below was applied onto the surface of the film to form thereon a layer having a dry thickness of 1 μm, thereby constructing a thermal transfer recording ink sheet of Example 201.

| (Dye-Donating Layer-Forming Coating Composition) | |
|---|---|
| Compound (Y-1) | 5.5 mas. pts. |
| Polyvinylbutyral Resin (Eslec BX-1, trade name by Sekisui Chemical Industry) | 4.5 mas. pts. |
| Methyl ethyl ketone/toluene (1/1) | 90 mas. pts. |

Comparative Examples 201, 201

Production of Thermal Transfer Recording Ink Sheet

Thermal transfer recording ink sheets of Comparative Examples 201 and 202 were produced in the same manner as in Example 201, for which, however, the Compound (Y-1) was changed to the following comparative compound (H-1) and (H-2). Comparative Compound (H-1) (similar to the compound described in JP-A S61-268760)

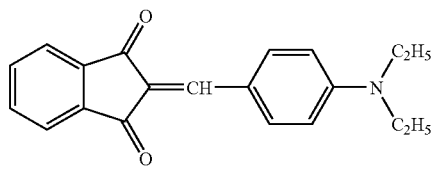

Comparative Compound (H-2) (similar to the compound described in Proceedings of SPIE—The International Society for Optical Engineering (1999), 3796(Organic Nonlinear Optical Materials), 202-208)

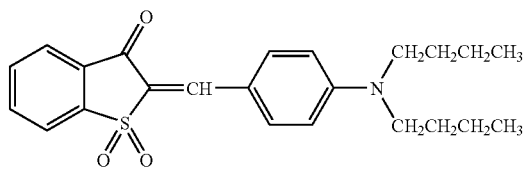

Example 301

Evaluation of Thermal Transfer Recording Ink Sheet, and Thermal Transfer Recording Image Formation According to Thermal Transfer Recording Method The thermal transfer recording ink sheet produced in Example 201, Comparative Example 201 and 202 constructed as above, and the image-receiving material for ASK2000 produced by FUJIFILM were combined in such a manner that the dye-donating layer could face the image-receiving layer, and this was printed using a thermal head applied to the back of the dye-donating material. The output power of the thermal head was 0.25 W/dot, pulse width was from 0.15 to 15 msec, the dot density was 6 dots/mm. In that manner, the yellow dye was imagewise fixed on the image-receiving layer of the image-receiving material, and as a result, a sharp image print with no transfer unevenness was obtained.

FIG. 1 shows a reflection spectrum of the recorded image obtained in Example 301. As is obvious from the result in FIG. 1, it is understood that the thermal transfer ink sheet of the invention has an excellent spectral characteristic with a sharp absorption and has an excellent property. It is also understood that the thermal transfer-recorded image obtained according to the thermal transfer recording method of the invention has an excellent spectral characteristic with a sharp absorption and has an excellent property.

Next, the recorded samples were exposed to an Xe light (17000 lux) for 5 hours, and tested for the light stability (light fastness) of the recorded images. After the exposure, regarding to the yellow part, the status A reflection density of the part of each sample having an original status A reflection density of 1.0 before the exposure was measured, and the retention (by percentage) to the reflection density of 1.0 after exposure to that before exposure indicates the image stability. With the retention percentage, the samples were ranked in three, A (from 70% to less than 100%), B (from 50% to less than 70%), C (less than 50%). The results are shown in Table 2 below.

TABLE 2

| Dye | Light Fastness |
|---|---|
| Example 201 | A |
| Comparative Example 201 | B |
| Comparative Example 202 | C |

Example 401

Formation of Color Toner 3 parts by mass of an dye compound of the invention produced in Example 101 (compound (Y-1)) and 100 parts by mass of a toner resin [styrene-acrylate copolymer, Himer TB-1000F (trade name by Sanyo Chemical)] were mixed and ground in a ball mill, then melted and kneaded under heat at 150° C., and after cooled, this was roughly ground with a hammer mill, and then finely ground with an air jet-type grinder. Further classified, particles of from 1 to 20 µm in size were selected to be a color toner of Example 401.

10 parts by mass of the color toner of Example 401 was uniformly mixed with 900 parts by mass of a carrier iron powder (EFV250/400, trade name by Nippon Iron Powder) to prepare a developer. The developer was tested for copying with a dry-type plain paper electrophotographic copier (NP-5000, trade name by Canon). As a result, the developer had excellent spectral characteristics and had excellent properties as toner.

Example 501

Formation of Inkjet Ink

A dye compound of the invention produced in Example 101 (compound (Y-1)) (5.63 g) and sodium dioctylsulfosuccinate (7.04 g) were dissolved in a high-boiling-point organic solvent mentioned below (S-2) (4.22 g), a high-boiling-point organic solvent mentioned below (S-11) (5.63 g) and ethyl acetate (50 ml) at 70° C. With stirring with a magnetic stirrer, deionized water (500 ml) was added to the solution to produce an oil-in-water crude particle dispersion.

Next, the crude particle dispersion was led to pass through a microfluidizer (by MICROFLUIDEX INC) five times under a pressure of 60 MPa to be fine particles, and the thus-prepared emulsion was evaporated for solvent removal with a rotary evaporator until it gave no ethyl acetate odor.

Diethylene glycol (140 g), glycerin (50 g), SURFYNOL 465 (trade name by Air Products & Chemicals) (7 g) and deionized water (900 ml) were added to the fine emulsion of the hydrophobic dye thus obtained as above, thereby producing an inkjet ink of Example 501.

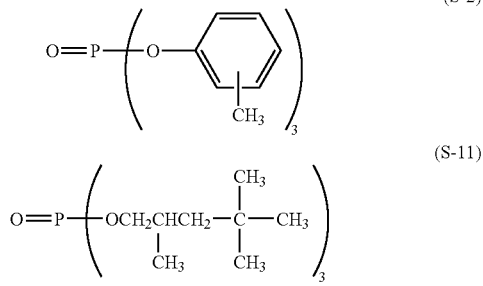

The thus-obtained inkjet ink of Example 501 was filled in a cartridge of an inkjet printer (PM-G800, trade name by Seiko Epson), and tested in the printer for image recording on inkjet paper, Kassai Photofinish Pro (trade name by FUJIFILM). The reflection spectrum of the thus-formed image is shown in FIG. 1. As is obvious from the data in FIG. 1, it is known that the obtained image has excellent spectral characteristics and the ink has excellent properties as inkjet ink.

Example 601

Construction of Color Filter (Preparation of Positive Resist Composition)

3.4 parts by mass of cresol/novolak resin obtained from a mixture of m-cresol/p-cresol/formaldehyde (reaction molar ratio=5/5/7.5) (polystyrene-based mass-average molecular weight, 4300), 1.8 parts by mass of o-naphthoquinonediazido-5-sulfonate ester produced by the use of a phenol compound having a formula mentioned below (in which 2 hydroxyl groups were esterified on average), 0.8 parts by mass of hexamethoxymethylolated melamine, 20 parts by mass of ethyl lactate, and 1 part by mass of the compound (Y-1) produced in Example 101 were mixed to produce a positive resist composition. Phenolic Compound:

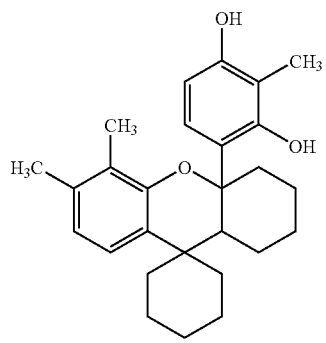

(Construction of Color Filter)

The obtained positive resist composition was applied onto a silicon wafer in a mode of spin coating, and the solvent was evaporated away. Next, the silicon wafer was exposed to light through a mask to decompose the quinonediazide compound. Next, this was heated at 100° C. and then the exposed area was removed by alkali development to obtain a positive color pattern having a resolution of 0.8 µm. This was exposed on the entire surface, and then heated at 150° C. for 15 minutes to produce a yellow-complementary color filter of Example 601. For the exposure, used was an i-ray exposure stepper HITACHI LD-5010-i (trade name by Hitachi, NA=0.40). As the developer, used was SOPD or SOPD-B (trade name by Sumitomo Chemical Industry).

Figure 2:
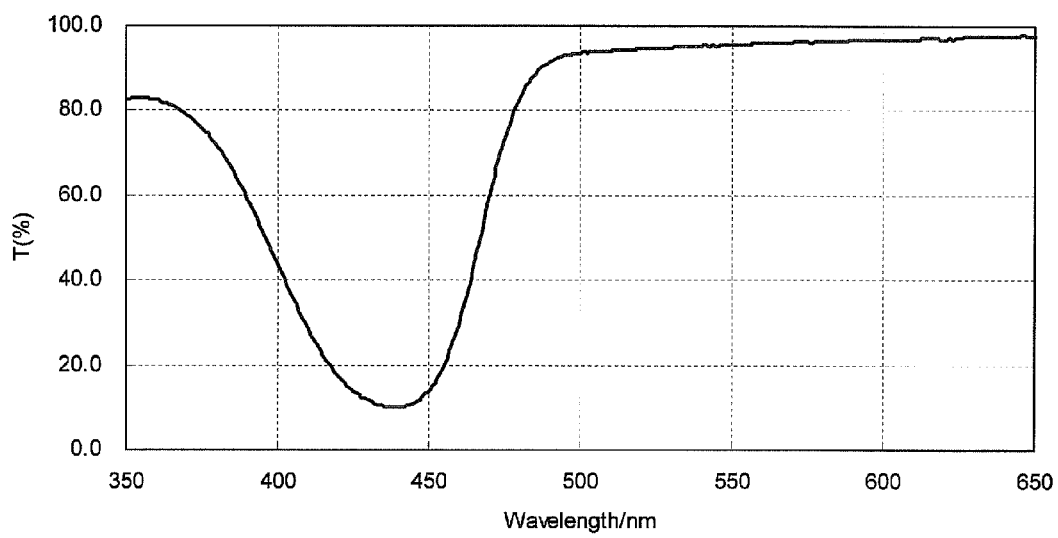
FIG. 2 is a transmission spectrum of the color filter produced in Example 601.

The transmission spectrum of the obtained color filter is shown in FIG. 2. As is obvious from the data in FIG. 2, the obtained color filter of Example 601 has excellent spectral characteristics and light transmittance, and has excellent properties as color filter.

According to the invention, there are provided a novel dye compound, and a coloring composition containing the dye compound. According to the invention, there are also provided a thermal transfer recording ink sheet and a thermal transfer recording method, a color toner, an inkjet ink and a color filter comprising the dye compound. Accordingly, the invention is expected to be effectively used in high-quality full color recording, and its industrial applicability is great.

The present disclosure relates to the subject matter contained in Japanese Patent Application No. 049977/2008 filed on Feb. 29, 2008, which is expressly incorporated herein by reference in its entirety. All the publications referred to in the present specification are also expressly incorporated herein by reference in their entirety.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined claims set forth below.

What is claimed is:

1. A dye compound of the following formula (3):

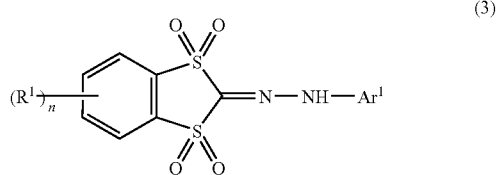

wherein $R^1$ represents a monovalent substituent; n indicates an integer of from 0 to 4; $Ar^1$ represents a group selected from the following aryl group and heterocyclic group (1); when n is 2 or more, then plural $R^1$'s may be the same or different;

Aryl group and heterocyclic group (1):

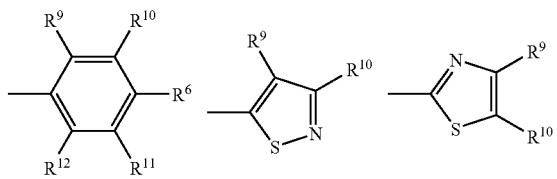

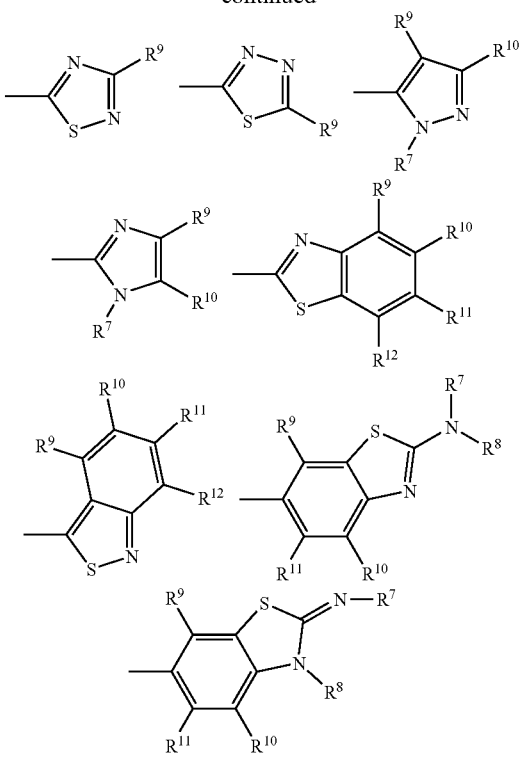

wherein R⁶ represents a monovalent substituent; and R⁷, R⁸, R⁹, R¹⁰, R¹¹ and R¹² each independently represents a hydrogen atom or a monovalent substituent.

2. The dye compound of claim 1, wherein R⁶ represents a substituted or unsubstituted amino group, a substituted or unsubstituted alkoxy group having from 1 to 8 carbon atoms, a substituted or unsubstituted alkylthio group having from 1 to 8 carbon atoms, a substituted or unsubstituted alkoxycarbonyl group having from 1 to 8 carbon atoms, a substituted or unsubstituted aryloxycarbonyl group having from 6 to 10 carbon atoms, a substituted or unsubstituted carbamoyl group, a cyano group, or a nitro group; R⁷ and R⁸ each independently represents a hydrogen atom, a substituted or unsubstituted alkyl group having from 1 to 8 carbon atoms, a substituted or unsubstituted aryl group having from 6 to 10 carbon atoms, or a substituted or unsubstituted heterocyclic group; and R⁹, R¹⁰, R¹¹ and R¹² each independently represents a hydrogen atom, a substituted or unsubstituted alkyl group having from 1 to 8 carbon atoms, a substituted or unsubstituted alkoxy group having from 1 to 8 carbon atoms, a substituted or unsubstituted aryl group having from 6 to 10 carbon atoms, a substituted or unsubstituted heterocyclic group, a substituted or unsubstituted acyl group, a substituted or unsubstituted alkoxycarbonyl group having from 1 to 8 carbon atoms, a substituted or unsubstituted amino group, a cyano group, a carbamoyl group, or a substituted or unsubstituted sulfo group.

3. The dye compound of claim 1, wherein R⁶ represents a substituted or unsubstituted amino group, a substituted or unsubstituted alkoxy group having from 1 to 8 carbon atoms, a substituted or unsubstituted alkylthio group having from 1 to 8 carbon atoms, a substituted or unsubstituted alkoxycarbonyl group having from 1 to 8 carbon atoms, a substituted or unsubstituted aryloxycarbonyl group having from 6 to 10 carbon atoms, a cyano group, or a nitro group; R⁷ and R⁸ each independently represents a hydrogen atom, a substituted or unsubstituted alkyl group having from 1 to 8 carbon atoms, or a substituted or unsubstituted aryl group having from 6 to 10 carbon atoms; and R⁹, R¹⁰, R¹¹ and R¹² each independently represents a hydrogen atom, a substituted or unsubstituted alkyl group having from 1 to 8 carbon atoms, a substituted or unsubstituted alkoxy group having from 1 to 8 carbon atoms, a substituted or unsubstituted phenyl group, a substituted or unsubstituted heterocyclic group, a substituted or unsubstituted acyl group, a substituted or unsubstituted alkoxycarbonyl group having from 1 to 8 carbon atoms, a substituted or unsubstituted amino group, a cyano group, a carbamoyl group, or a substituted or unsubstituted sulfo group.

4. The dye compound of claim 1, wherein Ar¹ is a phenyl group having a substituent, a substituted or unsubstituted isothiazolyl group, or a substituted or unsubstituted benzothiazolyl group, R¹ is a substituted or unsubstituted alkyl group having from 1 to 4 carbon atoms, and n is from 0 to 2.

5. A color toner containing a dye compound of the following formula (1'):

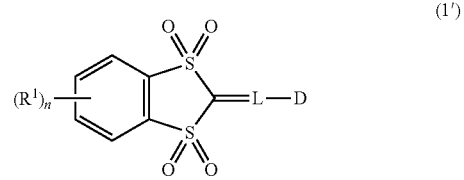

wherein D represents a substituted or unsubstituted aryl group, or a substituted or unsubstituted heterocyclic group; L represents =N— or =N—NH—; R¹ represents a monovalent substituent; R² represents a hydrogen atom or a cyano group; n indicates an integer of from 0 to 4; and when n is 2 or more, the plural R¹'s may be the same or different.

6. An inkjet ink containing a dye compound of the following formula (1'):

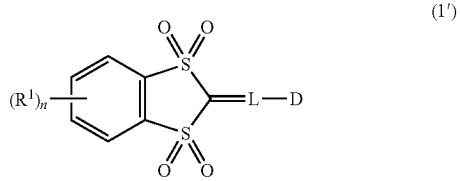

wherein D represents a substituted or unsubstituted aryl group, or a substituted or unsubstituted heterocyclic group; L represents =N— or =N—NH—; R¹ represents a monovalent substituent; R² represents a hydrogen atom or a cyano group; n indicates an integer of from 0 to 4; and when n is 2 or more, the plural R¹'s may be the same or different.

7. A color filter containing a dye compound of the following formula (1'):

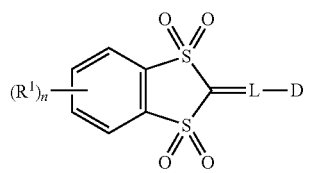

wherein D represents a substituted or unsubstituted aryl group, or a substituted or unsubstituted heterocyclic group; L represents =N— or =N—NH—; $R^1$ represents a monovalent substituent; $R^2$ represents a hydrogen atom or a cyano group; n indicates an integer of from 0 to 4; and when n is 2 or more, the plural $R^1$'s may be the same or different.

* * * * *